(12) United States Patent
Park et al.

(10) Patent No.: US 11,601,732 B2
(45) Date of Patent: Mar. 7, 2023

(54) DISPLAY SYSTEM FOR CAPSULE ENDOSCOPIC IMAGE AND METHOD FOR GENERATING 3D PANORAMIC VIEW

(71) Applicant: KOREA INSTITUTE OF MEDICAL MICROROBOTICS, Gwangju (KR)

(72) Inventors: Jong Oh Park, Gyeonggi-do (KR); Chang-Sei Kim, Gwangju (KR); Ayoung Hong, Daegu (KR); Eun Pyo Choi, Gwangju (KR); Hyun Seok Lee, Gwangju (KR); Hong Seok Choi, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 20 days.

(21) Appl. No.: 17/386,796

(22) Filed: Jul. 28, 2021

(65) Prior Publication Data

US 2022/0078343 A1 Mar. 10, 2022

(30) Foreign Application Priority Data

Sep. 7, 2020 (KR) .......................... 10-2020-0113682

(51) Int. Cl.
*H04N 13/221* (2018.01)
*H04N 23/698* (2023.01)
(Continued)

(52) U.S. Cl.
CPC ....... *H04N 23/698* (2023.01); *A61B 1/00009* (2013.01); *A61B 1/00048* (2013.01);
(Continued)

(58) Field of Classification Search
CPC .... H04N 5/23238; H04N 13/221; G06T 7/74; G06T 3/0093; A61B 1/00009; A61B 1/00048; A61B 1/041
See application file for complete search history.

(56) References Cited

U.S. PATENT DOCUMENTS

2003/0229268 A1* 12/2003 Uchiyama .......... A61B 1/00045
600/137
2008/0186378 A1* 8/2008 Shen ......................... G06T 7/38
348/E7.085

(Continued)

*Primary Examiner* — Thai Q Tran
*Assistant Examiner* — Jose M Mesa
(74) *Attorney, Agent, or Firm* — Harness, Dickey & Pierce, P.L.C.

(57) ABSTRACT

The present disclosure relates to a display system including a capsule image view, a 3D mini-map, and a 3D panoramic view, and a method of generating a 3D panoramic view. Specifically, according to the present disclosure, it is possible to infer the shape of an organ using a 3D mini-map and to simultaneously identify whether or not the capsule endoscope captures the images, and information on the position and posture of the capsule endoscope at primary captured points by visualizing the actual movement path of the capsule endoscope, thereby improving the accuracy of examination, and since multiple 2D images captured by a single capsule endoscope are able to be viewed as a single 3D panoramic image without changing the structure of the capsule endoscope, it is economical and the viewing angle of the image is able to be increased, thereby reducing the examination time and fatigue of the examiner.

7 Claims, 5 Drawing Sheets

(51) Int. Cl.
*A61B 1/00* (2006.01)
*G06T 7/73* (2017.01)
*G06T 3/00* (2006.01)
*A61B 1/04* (2006.01)

(52) U.S. Cl.
CPC ............ *A61B 1/041* (2013.01); *G06T 3/0093* (2013.01); *G06T 7/74* (2017.01); *H04N 13/221* (2018.05)

(56) References Cited

U.S. PATENT DOCUMENTS

| | | | |
|---|---|---|---|
| 2015/0334276 A1* | 11/2015 | Ecker | A61B 1/000094 348/76 |
| 2020/0138522 A1* | 5/2020 | Tikka | A61B 6/5247 |
| 2021/0004933 A1* | 1/2021 | Wong | G06T 7/248 |

* cited by examiner

DISPLAY SYSTEM FOR CAPSULE ENDOSCOPIC IMAGE AND METHOD FOR GENERATING 3D PANORAMIC VIEW

CROSS-REFERENCE TO RELATED APPLICATIONS

This application claims the benefit of and priority to Korean Patent Application No. 10-2020-0113682, filed on Sep. 7, 2020. The entire disclosure of the application identified in this paragraph is incorporated herein by reference.

FIELD

The present disclosure has been made, under the support of Ministry of Health and Welfare of South Korea, and assigned unique task number 1465031252 and task number HI19C0642010020. The dedicated research/management institute of this task is Korea Health Industry Development Institute, the research project name is "Development of practical medical microrobot platform", the research task name is "Development of a medical microrobot platform and visualization modules", the institute in charge is Korea Institute of Medical Microrobotics, and the research period is from Mar. 1, 2020 to Dec. 31, 2020.

The present disclosure relates to a display system including a capsule image view for reproducing an image captured by a capsule endoscope, a 3D mini-map for displaying a path of the capsule endoscope, position and posture information thereof, and a generation position of a 3D panoramic view, and a 3D panoramic view providing a wider angle of view than a capsule endoscopic camera, and further relates to a method for generating a 3D panoramic view.

BACKGROUND

A capsule endoscope indicates a capsule-type microscopic endoscope that enters a body cavity of an organ when swallowed by a patient like a pill, and allows doctors to directly observe the inside of the body cavity of the organ through a video screen or a computer monitor.

In general, capsule endoscope is one of endoscopies for taking pictures of organs in order for an examiner to examine the same without damaging the living body. The medical capsule endoscope has a small capsule shape, captures images inside a living body, and wirelessly transmits the captured images to an external storage device. The images captured by the endoscope are stored in a storage device. The images stored in the storage device are displayed on a display device through a conversion process, and the examiner observes the organs by viewing image data displayed on the display device.

However, since the capsule endoscope swallowed through the examinee's mouth for description continuously takes pictures of the internal surfaces of the organs such as the stomach, the small intestine, the large intestine, and the like for a predetermined period until it is naturally discharged from the examinee's living body, the capsule endoscope captures a large number of images. Therefore, the examiner must observe all the image data corresponding to the capturing time of the capsule endoscope and check whether or not there are lesions in the organs of the examinee, so it takes a long time for description.

In addition, it is a very arduous task for the examiner to check a large number of organ images captured by the capsule endoscope one by one, which may cause hasty description for the captured organ images, and thus may lead to errors in the examination results.

Although efforts are being made to reduce the time required for the description and fatigue of the examiner, there are still many problems with a loss of information on the original image data, difference in the image due to distortion of the boundary thereof in the image data, and the like.

In addition, although efforts are being made to improve the accuracy of description, it is impossible to recognize the position and posture of the capsule endoscope capturing the images in the living body because there is no spatial information, because it is difficult to compare image data captured at different times, and because information on the position and posture of the camera is not provided.

Therefore, a display system capable of reducing the fatigue of the examiner and description time by the examiner, thereby improving the convenience of description, as well as the accuracy of description, by processing a number of images captured by the capsule endoscope is urgently required to be developed.

SUMMARY

Accordingly, the present inventors have made efforts to make a display system capable of improving the convenience of the examiner and reducing the fatigue of the examiner and examination time by the examiner through conversion of a number of images captured by a capsule endoscope into 3D panoramic images to increase the examiner's viewing angle, and capable of enhancing the accuracy of examination by expressing a path on a 3D mini-map of the capsule endoscope to easily recognize the actually captured point.

As a result, it was confirmed that a display system including a 3D panoramic view has excellent effects of improving the convenience of the examiner and reducing the fatigue of the examiner and examination time by the examiner by increasing the examiner's viewing angle using a 3D panoramic view that provides a wider angle of view than a capsule endoscopic camera, and of enhancing the accuracy of examination by expressing a path on a 3D mini-map of the capsule endoscope to easily recognize the actually captured point.

Accordingly, an objective of the present disclosure is to provide a display system.

Another objective of the present disclosure is to provide a method for generating a 3D panoramic view.

The present disclosure relates to a display system including a capsule image view for reproducing an image captured by a capsule endoscope, a 3D mini-map for displaying a path of the capsule endoscope, position and posture information thereof, and a generation position of a 3D panoramic view, and a 3D panoramic view providing a wider angle of view than a capsule endoscopic camera, and further relates to a method for generating a 3D panoramic view.

Hereinafter, the present disclosure will be described in more detail.

An example of the present disclosure relates to a display system including: a storage unit configured to receive images captured by a capsule endoscope; a controller configured to transform the images into image data; a manipulation unit configured to generate a manipulation command; and a display unit configured to display the image data.

In the present disclosure, the storage unit 100 may receive and store images captured by the capsule endoscope.

In the present disclosure, the storage unit 100 may receive and store position and/or posture information of the capsule endoscope.

In the present disclosure, the capsule endoscope may include a capturing unit in order to take pictures of organs, but is not limited thereto.

In the present disclosure, the organs may be digestive organs, for example, any one or more selected from the group consisting of the esophagus, the stomach, the duodenum, the small intestine, and the large intestine, but is not limited thereto.

In the present disclosure, the capsule endoscope may determine an arbitrary position and posture in the direction independent of the movement direction of the capsule endoscope, and may take pictures of organs in the longitudinal direction and/or radial direction.

In the present disclosure, the capsule endoscope may include a position sensor device for obtaining position information of the capsule endoscope, but is not limited thereto.

In the present disclosure, the capsule endoscope may include a posture sensor device for obtaining posture information of the capsule endoscope, but is not limited thereto.

In the present disclosure, the capsule endoscope may further include a transmission device for transmitting, to the storage unit 100, position and/or posture information of the capsule endoscope during capturing images, but is not limited thereto.

In the present disclosure, the capsule endoscope may generate images by capturing images of organs, and, at the same time, may record position and/or posture information of the capsule endoscope at the time of capturing images in the captured images.

In the present disclosure, since the capsule endoscope records position and/or posture information of the capsule endoscope at the time of capturing images in the captured images, it is easy to compare images captured in the adjacent region with each other.

In the present disclosure, the controller 200 may transform the images captured by the capsule endoscope into image data, but is not limited thereto.

In the present disclosure, the image data may include any one or more selected from the group consisting of a capsule image view 410, a 3D mini-map 420, and a 3D panoramic view 430.

In an embodiment of the present disclosure, the image data may be the capsule image view 410.

In an embodiment of the present disclosure, the image data may be the 3D mini-map 420.

In an embodiment of the present disclosure, the image data may be the 3D panoramic view 430.

In the present disclosure, the controller 200 may receive a manipulation command from a manipulation unit 300.

In the present disclosure, the manipulation unit 300 may generate a manipulation command in order to manipulate image data displayed on a display unit 400.

In the present disclosure, the manipulation unit 300 may transmit the manipulation command to the controller 200 and/or the display unit 400.

In the present disclosure, the manipulation unit 300 may be configured as a separate device from the display unit 400, but is not limited thereto, and the manipulation unit 300 may be provided in the display unit 400, or may be provided on one surface of the display unit 400 in the case where the display unit 400 is configured as a touch screen.

In the present disclosure, the manipulation unit 300 may include at least one or more manipulation devices and/or at least one or more manipulation means.

In the present disclosure, the manipulation device may include a mouse, a joystick, and the like, but is not limited thereto.

In the present disclosure, the manipulation device may generate a manipulation command such as selecting a point on the display unit 400, dragging from one point to another point thereon, and the like.

In the present disclosure, the manipulation means may indicate a user interface (UI) provided in order to manipulate image data displayed on the display unit 400, but is not limited thereto.

In the present disclosure, the manipulation means may include a first manipulation means 310 that performs any one or more manipulations selected from the group consisting of play, fast forward, pause, rewind, and fast rewind.

In the present disclosure, the manipulation means may include a second manipulation means 320 that briefly displays the images captured by the capsule endoscope according to the time flow.

In the present disclosure, any one point on the second manipulation means 320 may be selected.

In the present disclosure, the second manipulation means 320 may display image data at the time corresponding to an arbitrary point on the display unit 400.

In an embodiment of the present disclosure, the second manipulation means 320 may include a capsule image view (general view) provision area 322, and/or a 3D panoramic view provision area 323.

In the present disclosure, the capsule image view provision area 322 may display an image at the time corresponding to the corresponding area on the capsule image view 410.

In the present disclosure, the 3D panoramic view provision area 323 may display an image at the time corresponding to the corresponding area on the capsule image view 410 and the 3D panoramic view 430.

In the present disclosure, the manipulation device may generate any one or more manipulation commands selected from the group consisting of selecting, enlarging, reducing, and rotating one point of image data.

In the present disclosure, the display unit 400 may include the capsule image view 410.

In the present disclosure, the capsule image view 410 may display an image captured by the capsule endoscope.

In the present disclosure, the capsule image view 410 may be enlarged or reduced according to any one or more manipulation commands selected from the group consisting of enlarging and reducing.

In the present disclosure, the capsule image view 410 may display movement from one point to another point on the capsule image by a manipulation command such as dragging from one point to another point and the like.

In the present disclosure, the display unit 400 may include the 3D mini-map 420.

In the present disclosure, the 3D mini-map 420 may display position and/or posture information of the capsule endoscope.

In the present disclosure, the 3D mini-map 420 may display a capsule endoscope path 421.

In the present disclosure, the capsule endoscope path 421 may indicate information on the path through which the capsule endoscope passes while capturing the images, but is not limited thereto.

In the present disclosure, the 3D mini-map 420 may be enlarged, reduced, or rotated according to any one or more manipulation commands selected from the group consisting of enlarging, reducing, and rotating.

In the present disclosure, the 3D mini-map 420 may display the movement from one point to another point on the capsule image by a manipulation command such as dragging from one point to another point and the like.

In the present disclosure, the capsule endoscope path 421 may display selection of any one point on the path by the manipulation command.

In the present disclosure, the capsule endoscope path 421 may display, on the display unit 400, the capsule image view 410 corresponding to any one point on the path.

In the present disclosure, the capsule endoscope path 421 may display, on the display unit 400, the 3D panoramic view 430 corresponding to any one point on the path.

In the present disclosure, the capsule endoscope path 421 may display position and/or posture information of the capsule endoscope corresponding to any one point on the path.

In the present disclosure, the 3D mini-map 420 may include a panoramic view generation point 422.

In the present disclosure, the panoramic view generation point 422 may indicate the point at which the 3D panoramic view 430 is generated.

In the present disclosure, the 3D panoramic view 430 may be obtained by transforming a 2D image captured by the capsule endoscope to a 3D panoramic image using the algorithm.

In the present disclosure, the 3D panoramic view 430 may be enlarged, reduced, or rotated by any one or more manipulation commands selected from the group consisting of enlarging, reducing, and rotating.

In the present disclosure, the 3D panoramic view 430 may the movement from one point to another point on the capsule image by a manipulation command such as dragging from one point to another point and the like.

In the present disclosure, the viewing angle of the 3D panoramic view 430 may be 120 to 360 degrees, 150 to 360 degrees, 180 to 360 degrees, 210 to 360 degrees, 240 to 360 degrees, 270 to 360 degrees, 300 to 360 degrees, or 330 to 360 degrees, and may be, for example, 330 to 360 degrees, but is not limited thereto.

In the present disclosure, the 3D panoramic view 430 may provide an image having a wider viewing angle than the viewing angle θ of the capsule endoscope, thereby increasing the convenience of the examiner and reducing the examination time.

In the present disclosure, the 3D panoramic image may be generated by grouping images captured by the capsule endoscope, extracting image feature points from the grouped images, calculating homography, and transforming the images into a warped image and a blended image, but is not limited thereto.

In the present disclosure, the term "homography" may indicate, when a plane including one diagram is projected onto another plane, a predetermined transformation relationship between corresponding points of the diagram included in the original plane and the diagram included in the projected plane.

In the present disclosure, the term "image feature point" may indicate a point in the image, which is invariant by the size, the rotation, the brightness, and the like, but is not limited thereto.

Another example of the present disclosure provides a method of generating a 3D panoramic view including the following steps: an image grouping step S200 of classifying the images captured by a capsule endoscope; a homography calculation step S210 of calculating a homography of the classified image; a homography transformation step S220 of transforming the classified image into a warped image using the homography; an image blending step S230 of transforming the warped image into a blended image; and a 3D-panoramic view generation step S240 of transforming the blended image into a 3D panoramic view.

In the present disclosure, the image grouping step S200 may indicate a step of classifying the images captured by the capsule endoscope according to position and/or posture information of the capsule endoscope.

In the present disclosure, the homography calculation step S210 may include a feature point-based homography calculation step S211.

In the present disclosure, the feature point-based homography calculation step S211 may indicate a step of extracting image feature points and a step of calculating the homography using the extracted image feature points.

In the present disclosure, the step of extracting the image feature points may include extracting the image feature points from the image using an algorithm such as Scale Invariant Feature Transform (SIFT), Fast stitching (FAST), Oriented BRIEF (ORB), or the like, but is not limited thereto.

In the present disclosure, the homography may indicate the correlation between the feature points in the image, but is not limited thereto.

In the present disclosure, the homography calculation step S210 may include calculating the homography from the image feature points using an algorithm such as Direct Linear Transformation (DLT) or Random Sample Consensus (RANSAC), but is not limited thereto.

In the present disclosure, the homography calculation step S210 may further include a capsule endoscope position and posture-based homography calculation step S212.

In the present disclosure, the capsule endoscope position and posture-based homography calculation step S212 may include calculating the homography of the image on the basis of position and/or posture information of the capsule endoscope.

In the present disclosure, the homography calculation step S210 may include calculating the homography through the capsule endoscope position and posture-based homography calculation step S212 when the homography fails to be calculated in the feature point-based homography calculation step S211.

In the present disclosure, the homography calculation step S210 may include calculating the homography by combining a first homography value calculated in the feature point-based homography calculation step S211 and a second homography value calculated in the capsule endoscope position and posture-based homography calculation step S212, thereby improving the accuracy in calculating the homography.

In the present disclosure, the homography transformation step S220 may be warping in which the homography of a plurality of images is mapped to pixels of a coordinate system in a spherical shape, a cylindrical shape, a plane shape, a fisheye shape, or the like and is projected into a planar image to be one panoramic image, but is not limited thereto.

In the present disclosure, the warping may be performed using an algorithm such as spherical projection, cylindrical projection, plane projection, or the like depending on the purpose of producing the panoramic image, but is not limited thereto.

In the present disclosure, the warped image may be an image obtained by mapping pixels on the coordinate system in a spherical shape, a cylindrical shape, a plane shape, a fisheye shape, or the like using the homography of a plurality of images and converting the image by projecting the same into the planar image to be a panoramic image, but is not limited thereto.

In the present disclosure, the image blending step S230 may include determining seam lines of a plurality of warped images (seam finder) and naturally transiting the current image to the next image on the basis of the seam lines, but is not limited thereto.

In the present disclosure, the image blending step S230 may be performed using an algorithm such as feature blending or multiband blending, but is not limited thereto.

In the present disclosure, the 3D panoramic view generation step S240 may include configuring image data of the blended image in a spherical shape, a cylindrical shape, a plane shape, a fisheye shape, or the like, but is not limited thereto.

The present disclosure relates to a display system including a capsule image view, a 3D mini-map, and a 3D panoramic view, and a method of generating a 3D panoramic view. Specifically, according to the present disclosure, it is possible to infer the shape of an organ using a 3D mini-map and to simultaneously identify whether or not the capsule endoscope captures the images, and information on the position and posture of the capsule endoscope at primary captured points by visualizing the actual movement path of the capsule endoscope, thereby improving the accuracy of examination.

In addition, since multiple 2D images captured by a single capsule endoscope are able to be viewed as a single 3D panoramic image without changing the structure of the capsule endoscope, it is economical and the viewing angle of the image is able to be increased, thereby reducing the examination time and fatigue of the examiner and increasing the convenience of examination.

DETAILED DESCRIPTION

The present disclosure may be variously modified, and may have various embodiments, so specific embodiments will be illustrated in the drawings, and will be described herein. However, this is intended only to describe the present disclosure in more detail, and it will be obvious to those of ordinary skill in the art that the scope of the present disclosure is not limited to the specific embodiments according to the subject matter of the present disclosure and encompasses all modifications, equivalents, and substitutes thereof included in the scope of the technical spirit of the present disclosure.

Hereinafter, an embodiment will be described in detail with reference to the accompanying drawings in which the same or corresponding element will be denoted by the same reference numeral throughout the drawings, and a redundant described will be omitted. In addition, it should be noted that terms indicating directions or positions such as up and down, left and right, front and back, and the like used below are based on the accompanying drawings.

Figure 1:
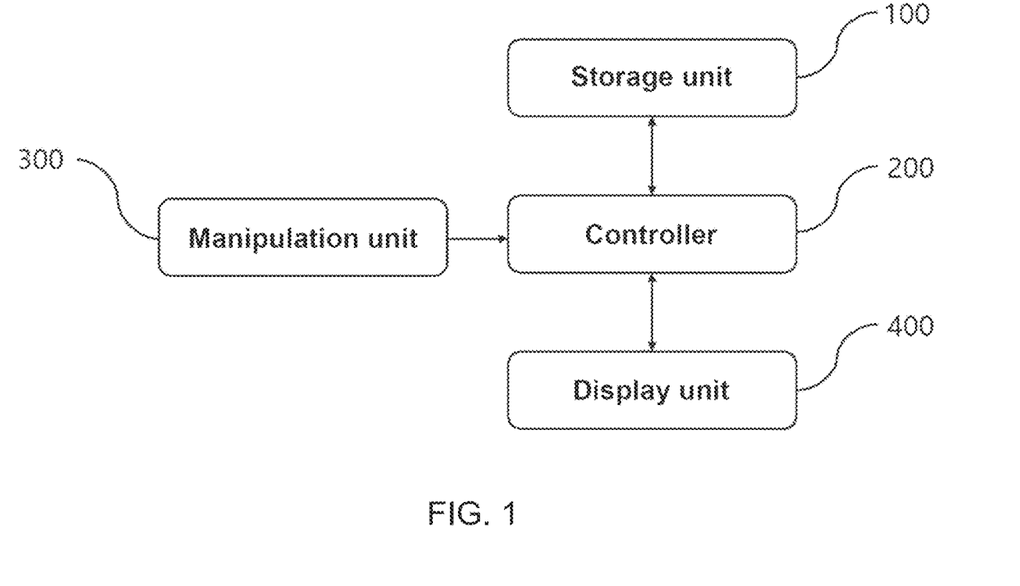
FIG. 1 is a block diagram illustrating a display system including a 3D panoramic view of the present disclosure.

FIG. 1 is a block diagram illustrating a display system according to an embodiment of the present disclosure.

Referring to FIG. 1, the display system may include a storage unit 100 that receives images captured by a capsule endoscope inserted into the living body and position and posture information of the capsule endoscope, a controller 200 that transforms an image into image data, a manipulation unit 300 that generates a manipulation command for manipulating image data, and a display unit 400 for displaying the image data.

The controller 200 may convert the images captured by the capsule endoscope into the capsule image view 410, the 3D mini-map 420, and the 3D panoramic view 430.

The 3D mini-map 420 may display information 421 on path through which the capsule endoscope passes, position and posture information of the capsule endoscope, and 3D panoramic view generation point information 422.

Using the 3D mini-map 420, the path through which the capsule endoscope passes after being inserted into the human body, position and posture information at the time of taking a picture of an organ surface, and a point, where the 3D panoramic view is generated, may be identified conveniently.

Figure 2:
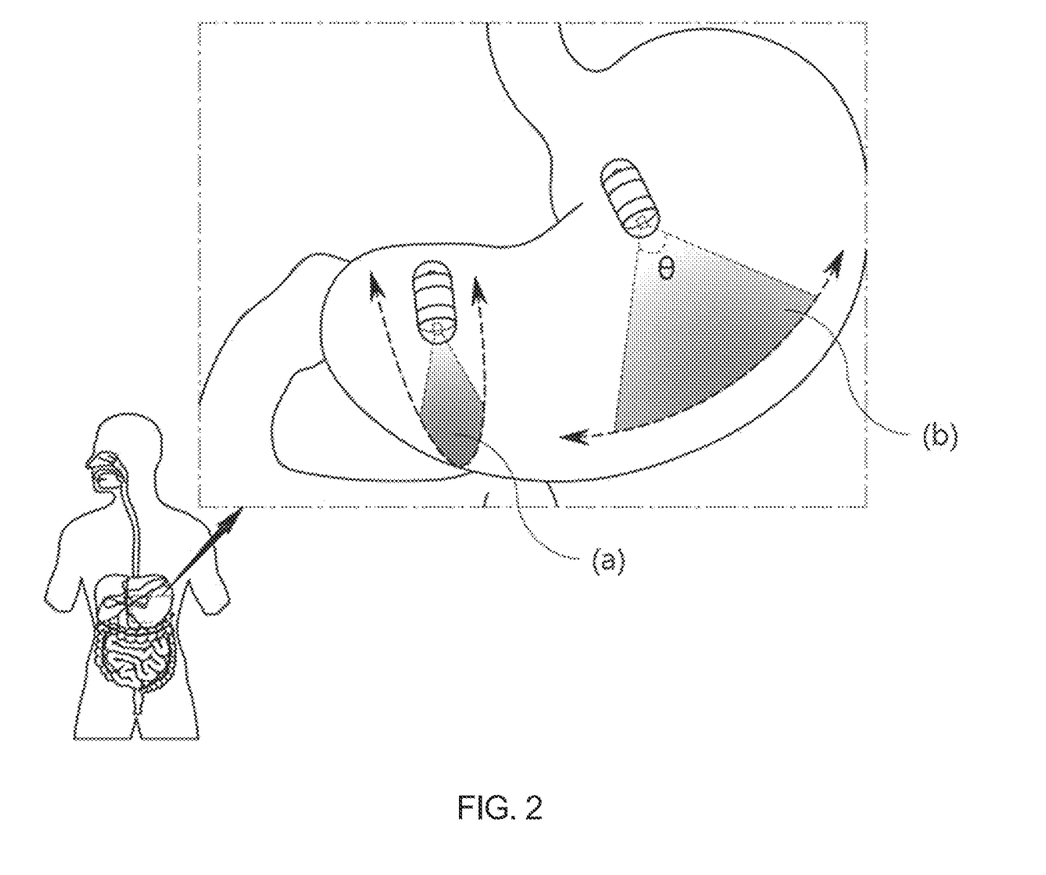
FIG. 2 is a virtual diagram illustrating the state in which the capsule endoscope takes pictures of organs in the longitudinal direction or radial direction according to an embodiment of the present disclosure.

FIG. 2 is a virtual diagram illustrating the state in which the capsule endoscope of the present disclosure takes pictures of organs in the longitudinal direction or radial direction.

Referring to FIG. 2, the capsule endoscope may determine arbitrary position and posture independently of the movement direction of the capsule endoscope to then capture images of the organs in the longitudinal direction (a) and/or radial direction (b).

The viewing angle θ of the capsule endoscope may be about 120 degrees.

In addition, the capsule endoscope of the present disclosure may input both position and posture information of the capsule endoscope into the captured images, thereby identifying both the captured images and the position and posture information of the capsule endoscope at the time of capturing the images.

Figure 3:
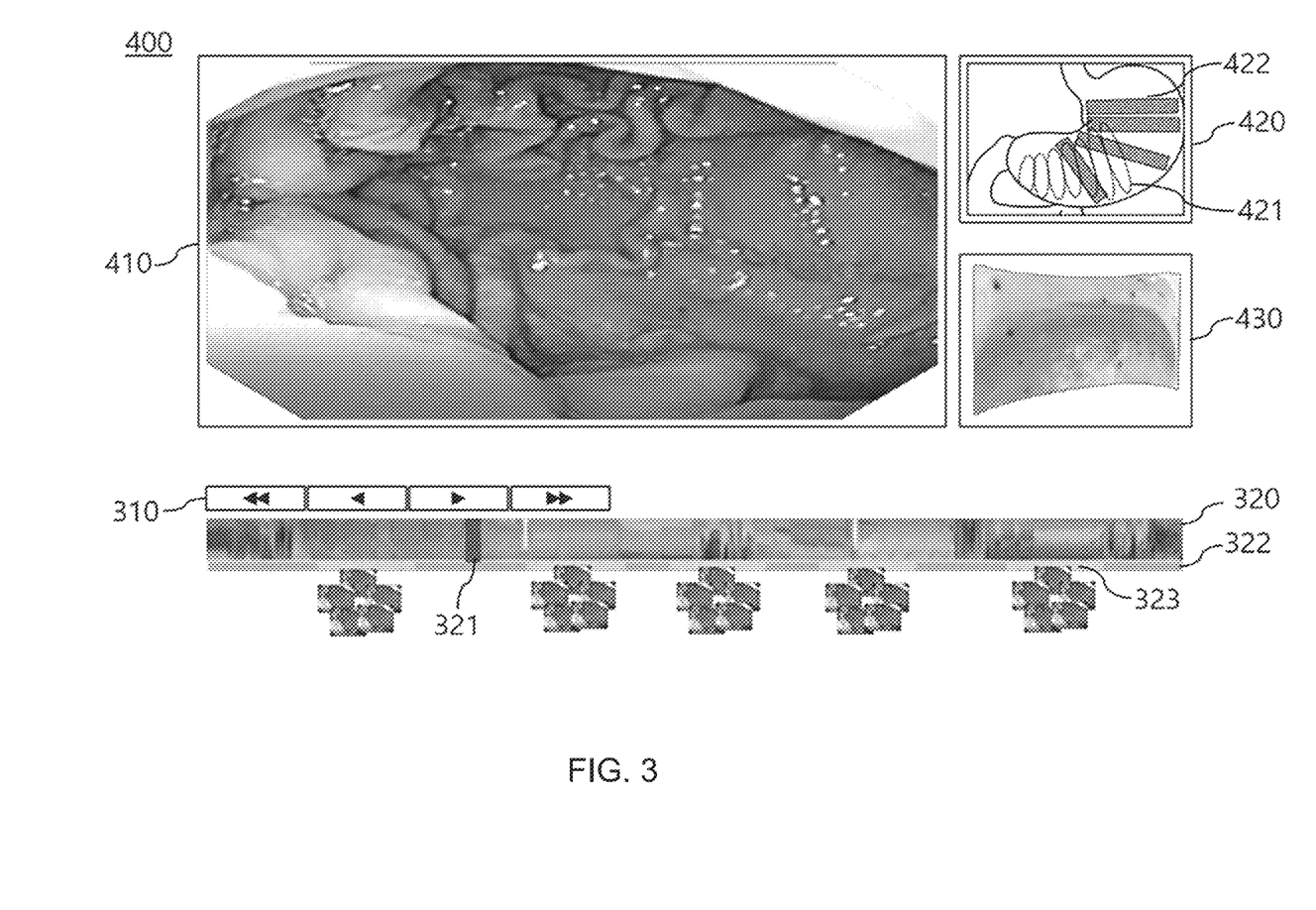
FIG. 3 is a virtual diagram illustrating a display unit according to an embodiment of the present disclosure.

FIG. 3 is a virtual diagram illustrating a display unit 400 according to an embodiment of the present disclosure.

Referring to FIG. 3, the display unit 400 may include a capsule image view 410, a 3D mini-map 420, and a 3D panoramic view 430, which reproduce the images captured by the capsule endoscope.

The 3D mini-map 420 may display a path 421 of the capsule endoscope, position and posture information of the capsule endoscope, and a 3D panoramic view generation point 422.

In addition, the display unit 400 may include a first manipulation means 310.

The first manipulation means 310 may enable manipulations such as play, fast forward, rewind, or fast rewind of image data.

In addition, the display unit 400 may include second manipulation means 320.

The second manipulation means 320 may briefly display the images captured by the capsule endoscope with a time flow, and, if an arbitrary point is selected by a manipulation command, may display image data corresponding to the time corresponding thereto on the display unit 400.

In addition, the second manipulation means 320 may include a current position display means 321, thereby identifying information on the time at which the image data displayed on the display unit 400 is captured.

In addition, the second manipulation means 320 may be divided into a capsule image view provision area 322 and/or a 3D panoramic view provision area 323.

A bundle of images disposed at the bottom of the 3D panoramic view provision area 323 may display images used to generate the 3D panoramic view 430.

The capsule image view 410 may perform manipulations such as enlarging and/or reducing according to a manipulation command.

The capsule image view 410 may perform manipulation such as dragging from one point to another point on the image, thereby moving the image.

This makes it possible to identify the capsule image that is too big to be displayed within the capsule image view 410.

In addition, the 3D mini-map 420 and the 3D panoramic view 430 may perform manipulation such as enlarging, reducing, and rotating according to the manipulation command.

The 3D mini-map 420 may perform manipulation such as dragging from one point to another point on the image or the like, thereby moving or rotating the image.

This makes it possible to identify a mini-map that is too big to be displayed within the 3D mini-map 420.

The 3D panoramic view 430 may perform manipulation such as dragging from one point to another point on the image or the like, thereby moving or rotating the image.

This makes it possible to identify a 3D panoramic image that is too big to be displayed within the 3D panoramic view 430.

Figure 4:
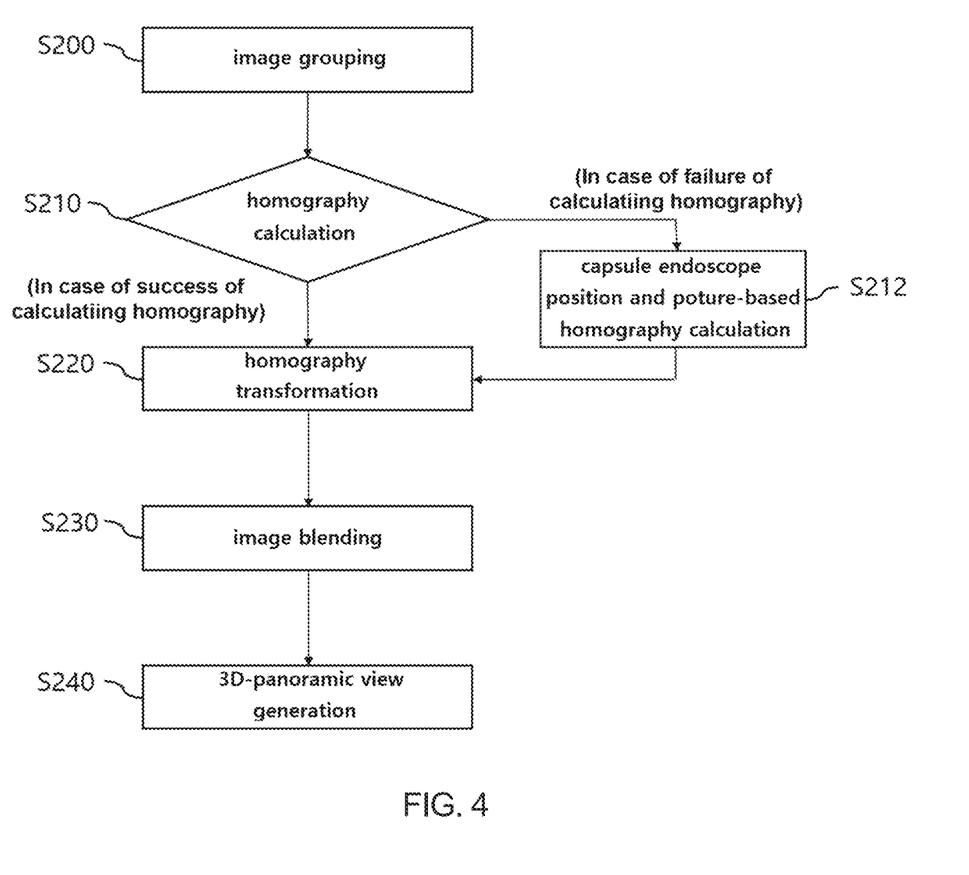
FIG. 4 is a block diagram illustrating a method of generating a 3D panoramic view according to the present disclosure.

FIG. 4 is a block diagram illustrating a method of generating a 3D panoramic view 430 according to an embodiment of the present disclosure.

Referring to FIG. 4, the method of generating the 3D panoramic view 430 may include: an image grouping step S200 of classifying the images captured by a capsule endoscope according to position and posture information of the capsule endoscope; a homography calculation step S210 of calculating homography of the classified image; a homography transformation step S220 of transforming the image into a warped image using the homography; an image blending step S230 of transforming the warped image into a blended image; and a 3D-panoramic view generation step S240 of transforming the blended image into a 3D panoramic view.

The image grouping step S200 may be classifying the images captured by the capsule endoscope according to position and posture information of the capsule endoscope.

The homography calculation step S210 may include a feature point-based homography calculation step S211 of extracting image feature points and calculating the homography using the extracted image feature points.

However, if the extraction of the image feature points fails, the homography calculation step S210 may perform a capsule endoscope position and posture-based homography calculation step S212.

Accordingly, a 3D panoramic view generating method of the present disclosure enables calculation of the accurate homography using the position and posture information of the capsule endoscope even in the case where the extraction of the image feature points fails due to a blur or unclarity in part of the image captured by the capsule endoscope.

In addition, even if the extraction of the image feature points is successful, the capsule endoscope position and posture-based homography calculation step S212 may be performed, and a first homography value based on the feature points and a second homography value based on the position and posture of the capsule endoscope may be combined to calculate a more accurate homography.

The homography transformation step S220 may be warping in which pixels are mapped to a coordinate system in a spherical shape, a cylindrical shape, a plane shape, a fisheye shape, or the like using the homography of a plurality of images and are projected into a planar image to be one panoramic image.

The image blending step S230 may include determining seam lines of the warped images (seam finder) and blending the images such that the current image naturally transits into the next image on the basis of the seam lines.

The 3D panoramic view generation step S240 may be configuring image data of the blended images in a spherical shape, a cylindrical shape, a plane shape, a fisheye shape, or the like.

Figure 5:
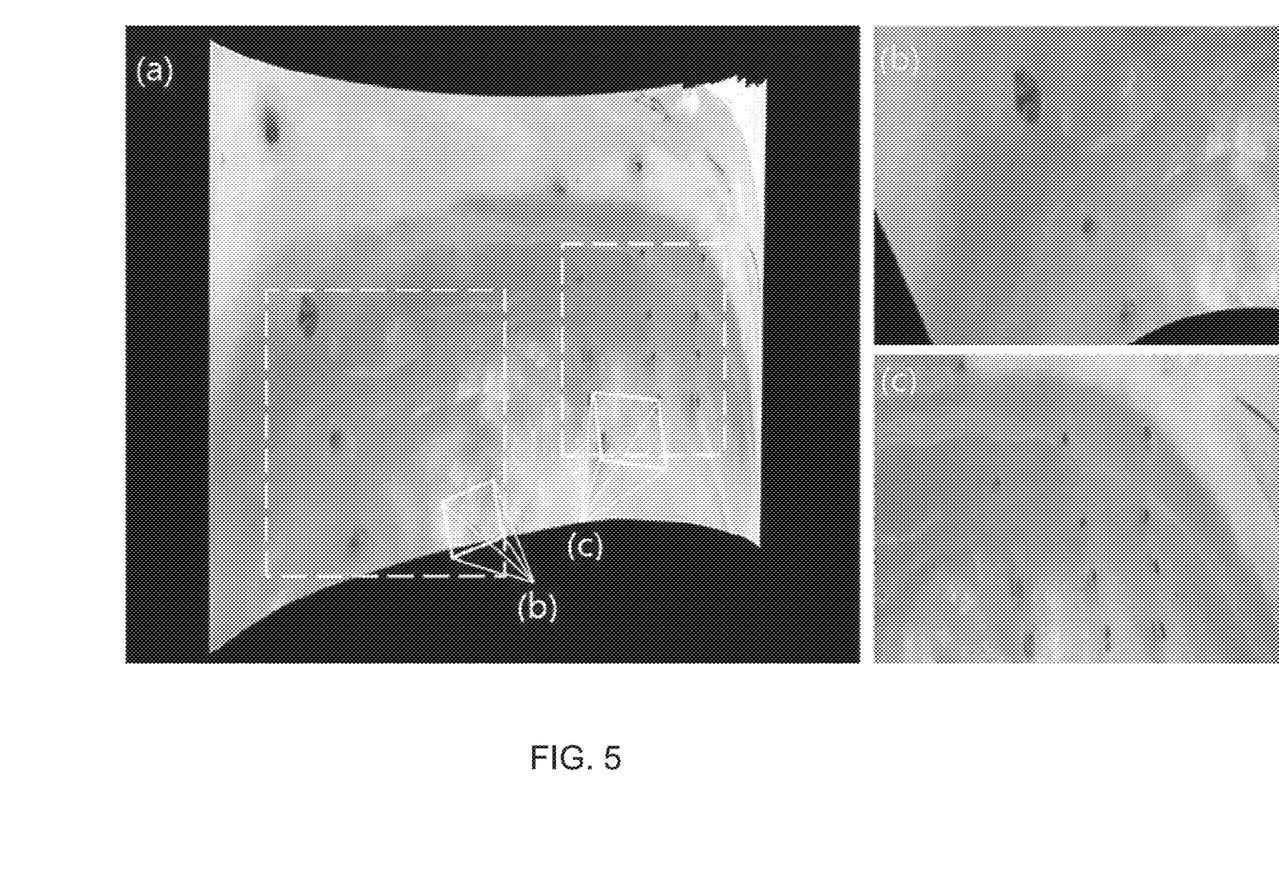
FIG. 5 is a virtual diagram illustrating the state in which a 3D panoramic view is generated by re-projecting 2D images according to an embodiment of the present disclosure.

FIG. 5 is a virtual diagram illustrating the state in which a 3D panoramic view is generated by re-projecting 2D images according to an embodiment of the present disclosure.

Referring to FIG. 5, (a) may indicate the 3D panoramic view 430, and (b) and (c) may indicate arbitrary regions specified and enlarged in the 3D panoramic view.

EXPLANATION OF MARKS

100: storage unit
200: controller
300: manipulation unit
310: first manipulation means
320: second manipulation means
321: current position display means
322: capsule image view provision area
323: 3D panoramic view provision area
400: display unit
410: capsule image view
420: 3D mini-map
421: capsule endoscope path
422: panoramic view generation point
430: 3D panoramic view
S200: image grouping step
S210: homography calculation step
S211: feature point-based homography calculation step (not-illustrated)
S212: capsule endoscope position and posture-based homography calculation step
S220: homography transformation step
S230: image blending step
S240: 3D panoramic view generation step

What is claimed is:

1. A display system comprising:
a storage unit configured to receive images captured by a capsule endoscope;
a controller configured to convert the images into image data;
a manipulation unit configured to generate a manipulation command; and
a display unit configured to display the image data,
wherein the capsule endoscope determines an arbitrary position and posture in the direction independent of the movement direction of the capsule endoscope, and
the capsule endoscope further comprises a posture sensor device for obtaining posture information of the capsule endoscope,
wherein the images captured by the capsule endoscope comprise position information and posture information of the capsule endoscope,
wherein the image data further comprise a capsule image view and a 3D mini-map,
wherein the 3D mini-map is configured to display position information and posture information of the capsule endoscope.

2. The display system of claim 1, wherein the image data further comprises a 3D panoramic view.

3. The display system of claim 2, wherein the 3D mini-map is configured to further display path information of the capsule endoscope or 3D-panoramic view generation point information.

4. The display system of claim 2, wherein the 3D panoramic view has a viewing angle of 120 to 360 degrees.

5. The display system of claim 1, wherein the manipulation unit comprises a first manipulation means, and wherein the first manipulation means performs any one or more operations selected from the group consisting of play, fast-forward, rewind, and fast-rewind of the image data.

6. The display system of claim 1, wherein the manipulation unit comprises a second manipulation means, and
wherein the second manipulation means is configured to display the image data at the time corresponding to an arbitrary point on the display unit.

7. A method of generating a 3D panoramic view, the method comprising:
an image grouping step of classifying the images captured by a capsule endoscope;
a homography calculation step of calculating homography of the classified images;
a homography transformation step of transforming the classified image into a warped image using the homography;
an image blending step of converting the warped image into a blended image; and
a 3D-panoramic view generation step of converting the blended image into a 3D panoramic view,
wherein the homography calculation step, which is calculating homography by combining a first homography and a second homography, comprises:
a first homography calculation step of calculating homography using image feature points of the image; and
a second homography calculation step of calculating homography using position and posture information of the capsule endoscope.

* * * * *